United States Patent [19]

Lau et al.

[11] Patent Number: 4,649,207

[45] Date of Patent: Mar. 10, 1987

[54] DERIVATIVES OF DIPHENYLHEXAFLUOROPROPANE

[75] Inventors: Kreisler S. Y. Lau, Alhambra; William J. Kelleghan, Santa Monica, both of Calif.

[73] Assignee: Hughes Aircraft Company, Los Angeles, Calif.

[21] Appl. No.: 862,742

[22] Filed: May 13, 1986

Related U.S. Application Data

[63] Continuation-in-part of Ser. No. 646,999, Sep. 4, 1984, abandoned.

[51] Int. Cl.$^4$ .................. C07C 63/33; C07C 49/76; C07C 47/52; C07C 25/18
[52] U.S. Cl. ...................... 549/563; 585/25; 585/320; 556/465; 556/485; 556/487; 562/491; 568/331; 568/425; 570/129; 570/144
[58] Field of Search ............... 585/320, 25; 556/465, 556/485, 487, 488; 549/563; 562/491; 568/331, 425; 570/129, 144

[56] References Cited

U.S. PATENT DOCUMENTS 3,310,573 3/1967 Coe ........................................ 564/442
4,374,291 2/1983 Lau ........................................ 585/320
4,503,254 3/1985 Kelleghan ........................... 570/144

FOREIGN PATENT DOCUMENTS 1228007 4/1971 United Kingdom .

OTHER PUBLICATIONS

Chemical Abstracts 89:180690u, "Dielectric Properties of Glass-Fabric Laminates Based on Halogen-Containing Epoxy Resins", Shirokov et al, (1978).
Chemical Abstracts 102:114582w, "Impact-Resistant Matrix Resins for Advanced Composites", Gardner et al, (1985).

Primary Examiner—Morton Foelak
Assistant Examiner—Nathan M. Nutter
Attorney, Agent, or Firm—M. E. Lachman; A. W. Karambelas

[57] ABSTRACT

Derivatives of diphenylhexafluoropropane having the formula:

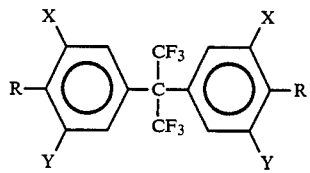

where R is an unsubstituted or substituted alkylene, an epoxy, a silyl or alkoxysilyl group; and where X and Y are hydrogen or halogen. The derivatives are useful in formulating polymer structures.

6 Claims, No Drawings

DERIVATIVES OF DIPHENYLHEXAFLUOROPROPANE

This application is a continuation-in-part of U.S. patent application Ser. No. 646,999, filed Sept. 4, 1984, and now abandoned.

BACKGROUND OF THE INVENTION

1. Field of the Invention

The present invention relates generally to diphenylhexafluoropropane derivatives and, more particularly, to derivatives wherein various groups are attached to the para-position on the phenyl rings of the diphenylhexafluoropropane by way of a carbon or silicon attachment.

2. Description of the Background Art

Diphenylhexafluoropropane is a very versatile compound which basically consists of two phenyl rings which are attached on opposite sides of the number two carbon of hexafluoropropane. In the past, a number of different derivatives of diphenylhexafluoropropane have been produced by attaching various different functional groups at either the para- or the meta- positions on the phenyl rings. These derivatives have proven to be useful intermediates in the synthesis of thermally stable resins for use in high temperature structural composites.

Diphenylhexafluoropropane compounds have been produced where various different functional groups, such as ethynyl groups, amino groups, or halogens, are attached to the phenyl rings at the meta- position by way of carbon or nitrogen linkages. As is well known, the specific isomeric form of chemical precursors and intermediates is an important factor in determining the final characteristics and performance of the desired chemical product. Accordingly, it has been desirable to also prepare diphenylhexafluoropropane derivatives in which the functional groups are attached to the phenyl rings at the para- position instead of the meta- position.

Diphenylhexafluoropropane compounds having an ethynyl group or a substituted ethynyl group attached at the para- or meta- position have been developed and are disclosed in U.S. Pat. No. 4,374,291 and U.S. patent application Ser. No. 466,271, respectively, both of which are assigned to the present assignee. However, other para-substituted diphenylhexafluoropropane derivatives which have been developed in the past and which are presently available all include an oxygen or sulfur linkage between the functional group and the phenyl ring. The attachment of the functional groups to the para-position on the phenyl rings via sulfur or oxygen results in a relatively flexible linkage which, in turn, tends to produce relatively flexible polymer products. Although flexible high temperature polymers are well suited for a variety of applications, it is many times desirable to provide thermally stable resins which have increased rigidity. Further, sulfur and oxygen linkages in polymer resins are more susceptible to oxidative degradation or breakdown resulting in premature deterioration of the polymer in which the sulfur or oxygen linked diphenylhexafluoropropane derivative is incorporated.

Therefore, there is a present need to provide para-substituted diphenylhexafluoropropane derivatives which can be used as alternate polymer precursors to meta-substituted derivatives and which do not include a sulfur or oxygen linkage between the para-substituted group and the phenyl rings.

SUMMARY OF THE INVENTION

In accordance with the present invention, a new group of para-substituted diphenylhexafluoropropane compounds are disclosed which provide an alternative polymer precursor to the meta-substituted diphenylhexafluoropropane derivatives while not requiring an oxygen or sulfur linkage.

The new diphenylhexafluoropropane derivatives have the following formula:

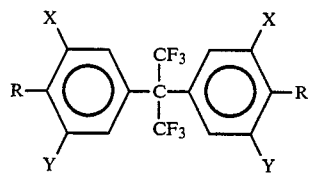

where R is an unsubstituted or substituted alkylene, an epoxy, a silyl or alkoxysilyl group; and where X and Y are hydrogen or halogen.

The diphenylhexafluoropropane derivatives in accordance with the present invention have a direct carbon or silicon linkage between the functional groups R and the phenyl rings of the diphenylhexafluoropropane. Carbon or silicon linkages are more rigid than sulfur or oxygen. As a result, more rigid polymers can now be produced from para-substituted diphenylhexafluoropropane than was previously possible with prior sulfur and oxygen linked derivatives. The new diphenylhexafluoropropane derivatives are not only useful in preparing rigid polymers, but the resulting polymers are also thermally stable and resistant to oxidative attack due to the absence of sulfur or oxygen linkages.

The above-discussed and many other features and attendant advantages of the present invention will become better understood by reference to the following detailed description of the invention.

DETAILED DESCRIPTION OF THE INVENTION

The compounds in accordance with the present invention have the following general formula

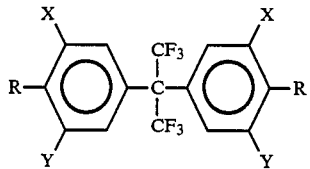

where R is an unsubstituted or substituted alkylene, an epoxy, a silyl or alkoxysilyl group; and where X and Y are hydrogen or halogen.

Preferred alkylene groups include from 1 to 4 carbon atoms. Vinyl and vinyl derivative groups are particularly preferred and include vinyl, β-chlorovinyl, β-methylvinyl, (β-acetoxy)vinyl, β-phenylvinyl, β, β-dimethylvinyl, α-chlorovinyl, (β-methoxycarbonyl-β-methyl)vinyl, in which the C≡C linkage is attached to the phenyl ring at the position indicated by R in the formula noted above.

Aryl groups having 1 or 2 phenyl rings are preferred. Silyl and alkoxysilyl groups having from 1 to 4 carbon atoms are preferred with trimethylsilyl and trimethoxysilyl being particularly preferred. In addition, any of the above-mentioned alkylene, silyl, or alkoxysilyl groups may include one or two phenyl rings.

In addition to the R groups attached at the para-position, the new compounds may include a halogen substituted at the meta-position. Any of the halogens may be used with iodine and bromine being preferred. Both X and Y may be a halogen if desired; however, it is preferred that when X is a halogen, Y is hydrogen. Also preferred are compounds where both X and Y are hydrogen.

The preparation of compounds in accordance with the present invention preferably begins with 2,2-bis(4-bromophenyl)hexafluoropropane (BPHP). BPHP is a reactive monomer which is described in U.S. Pat. No. 4,503,254, which has been assigned to the same assignee of the present invention. Although the preferred starting material is bromine substituted, the other para-halogenated substituted compounds set forth in U.S. Pat. No. 4,503,254, such as 2,2-bis(4-iodophenyl)hexafluoropropane and 2,2-bis(4-chlorophenyl)hexafluoropropane, may be used.

The 2,2-bis(4-bromophenyl)hexafluoropropane which is the starting compound in most of the following examples is prepared by reacting triphenylphosphine dibromide with Bisphenol AF [2,2-bis(4-hydroxyphenyl)-hexafluoropropane] at temperatures above 280° C. Bisphenol AF is a common compound which is widely available commercially. An exemplary synthesis is as follows:

To a slurry of triphenylphosphine dibromide (0.2 mole) in dichloromethane (250 ml) under argon was added 2,2-bis(4-hydroxyphenyl)hexafluoropropane (0.1 mole). The solvent was removed by distillation to leave a solid reaction mixture, and the flask which contained the reaction mixture was placed in a molten metal bath at 350° C. for two hours. The reaction mixture was cooled to 100° C. and poured into another flask. Further cooling of the reaction mixture resulted in a solid within the flask which was washed three times with 300 ml portions of hexane, and the hexane solution was filtered to remove unwanted reaction by-products. The resulting hexane solution of the product was washed with 20% sodium hydroxide and deionized water. The solution was then dried over anhydrous magnesium sulfate and passed down a short alumina column. The hexane was removed from the solution and the resulting semisolid was distilled to produce a 76% yield of the product 2,2-bis(4-bromophenyl)hexafluoropropane, which is a high yield for reactions of this nature.

Examples of preparation of preferred diphenylhexafluoropropane derivatives are as follows:

EXAMPLE 1

2,2-bis(4-trimethylsilylphenyl)hexafluoropropane

The synthesis is shown schematically as follows:

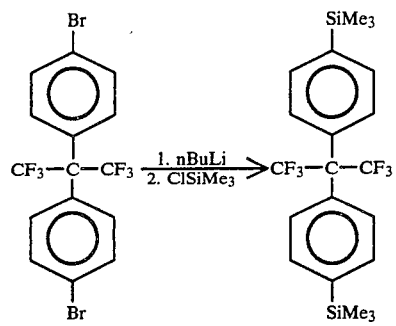

To a solution of 4.62g (0.1 mole) 2,2-bis(4-bromophenyl)hexafluoropropane in 75 ml of anhydrous tetrahydrofuran was added dropwise 28 ml (0.4 moles) of a 1.4 molar solution of n-butyllithium in hexane while the reaction mixture was cooled in a dry ice-acetone slush. The reaction mixture was stirred for one half hour at −78° C. A dropwise addition of chlorotrimethylsilane (5 ml, 0.04 moles) was then made to the reaction mixture at −78° C. The stirring slurry was allowed to come to ambient temperature over 16 hours. To the reaction mixture was added 100 ml hexane. The organic layer was washed with 2×150 ml saturated sodium chloride solution and 2×150 ml water. The organic layer was dried, filtered, and concentrated to yield the white crystalline product 2,2-bis(4-trimethylsilylphenyl)hexafluoropropane.

The following physical data were recorded:

NMR (CDCl$_3$): δ 7.4 (m, 4H, aromatic) and 0.5 ppm (s, 9H, silylmethyl).

IR (film): 2970, 1325, 1255, 1210, 1180, 970, 840, 815 cm$^{-1}$.

EXAMPLE 2

2,2-bis(4-vinylphenyl)hexafluoropropane

The synthesis is shown schematically as follows:

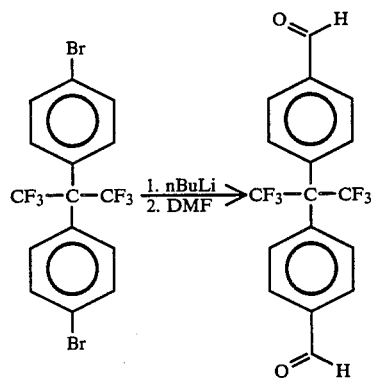

-continued

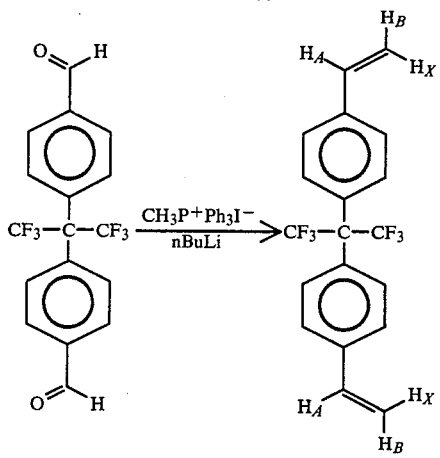

First, 2,2-bis(4-formylphenyl)hexafluoropropane was prepared as follows. To a solution of 17.58 g (0.38 moles) of 2,2-bis(4-bromophenyl)hexafluoropropane in 100 ml anhydrous tetrahydrofuran (THF) at −70° C. was added dropwise 83 ml of a 1.1 molar solution in hexane of n-butyllithium. The addition took thirty minutes. After 15 minutes at −60° to −65° C., a dropwise addition of 10.0 g (0.137 mole) of dimethylformamide in 50 ml anhydrous tetrahydrofuran was made to the reaction mixture. The reaction mixture was warmed to 25° C. over one hour and maintained at 25° C. for eighteen hours. At the end of this period, the reaction mixture was poured into 1 liter of stirred water. The product was extracted with ethyl ether, washed with 2×200 ml water and the ethereal layer dried. Concentration of the ethereal fraction afforded 8.46 g (23.5 moles, 61.8% yield) of the white solid product 2,2-bis (4-formylphenyl)hexafluoropropane, M. P. 130°-132° C.

Methyl triphenylphosphonium iodide (8.08 g) was suspended in 50 ml anhydrous tetrahydrofuran under argon. After cooling to −78° C. the slurry was treated with 20 ml (24 mMoles) of 1.2M n-butyllithium. After stirring for 15 minutes, a solution of the dialdehyde product formed as described above, in 40 ml tetrahydrofuran was added to the slurry still at −78° C. After completion of the addition, the reaction mixture was warmed to 25° C. over two hours and maintained at this temperature for 20 hours. The reaction mixture was poured into 500 ml of 10% hydrochloric acid. The product was extracted by four 100 ml ether washes. The combined ethereal extracts were washed with 200 ml of saturated sodium chloride solution and dried over magnesium sulfate. Concentration of the dried ether solution yielded a yellow oil. Column chromatography of this oil using silica gel and 10% methylene chloride in hexane yielded 1.370 g (38.5% yield) of a clear yellow viscous oil which was determined to be 2,2-bis(4-vinylphenyl)hexafluoropropane.

The following physical data were recorded:
GC-MS: one peak, m/e 356.
NMR (CDCl$_3$): δ b 7.3 (bs, 4H, aromatic H's), 6.9, 6.7, 6.6, 6.5 (d×d, 1H, $J_{AB}$=17.5 Hz, $J_{AC}$=11 Hz, vinyl H$_A$), 5.8, 5.6, (d×d, 1H, $J_{AB}$=17.5 Hz, $J_{BC}$=1.5 Hz, vinyl H$_B$), and 5.3, 5.1 ppm (d×d, 1H, $J_{AC}$=11 Hz, $J_{BC}$=1.5 Hz, vinyl H$_C$). The three vinyl protons give a classical ABX three-nuclei splitting pattern.

EXAMPLE 3

2,2-bis(4-epoxyphenyl)hexafluoropropane

The synthesis is shown schematically as follows:

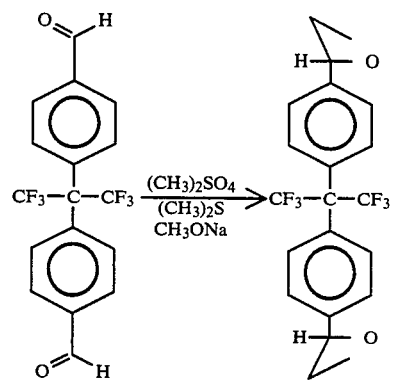

First, 2,2-bis(4-formylphenyl)hexafluoropropane was prepared as described with regard to Example 2. Next, in a flask with an argon atmosphere was placed 3.78 g (0.03 mole) dimethyl sulfate, 1.05 g (0.033 mole) dimethyl sulfide, and 20 ml acetonitrile. The mixture was stirred 24 hours at 25° C. Sodium methoxide (1.87 g, 0.033 mole) was added in one portion and the reaction mixture stirred another hour at 25° C. To the reaction mixture was then added 3.60 g (0.01 mole) 2,2-bis(4-formylphenyl)hexafluoropropane, formed as indicated above, over 15 minutes. After the addition was complete, the stirring was maintained for 18 hours. The reaction flask was then equipped for distillation and the majority of the dimethyl sulfide and dimethyl sulfate removed. To the cooled reaction product was added 20 ml acetonitrile. The organic layer was washed with 4×100 ml deionized water, dried over magnesium sulfate, concentrated, and purified using a Kugelrohr apparatus to obtain 2.21 g, 0.0057 moles, 57% yield of the product 2,2-bis(4-epoxyphenyl)hexafluoropropane.

The following physical data were recorded:
IR (film): 1270, 1250, 1215, 1185, 975, 885, 835 cm$^{-1}$.
NMR (CDCl$_3$): φ 7.3 (s), 5.6 (s), 3.8 (m), 3.1 (m), 2.7 (m) ppm.

The diphenylhexafluoropropane derivatives of this invention are useful in a large number of applications. The vinyl and epoxy derivatives may be used alone to produce homopolymer resin systems or they may be blended and subsequently copolymerized with known commercial resins such as any of the polyethylene, polystyrene, polybutadiene or similar common resins. (The term "resin" is used herein to designate a mixture of polymerizable materials either before or after polymerization.) The ease of vinyl and epoxy polymerization and the special structural characteristics of the vinyl (Example 2) and epoxide (Example 3) derivatives of the present invention jointly provide a facile entry to vinyl and epoxy resins which have the desirable low dielectric constant and low dissipation loss properties for electronic applications. Known polymerization methods may be used to polymerize the monomer compounds of the present invention.

An exemplary polymer which can be made utilizing the diphenylhexafluoropropane derivatives of the present invention and the method for preparing it are as follows:

EXAMPLE 4

Copolymer of Epoxidized Polybutadiene and 2,2-bis(4-epoxyphenyl)hexafluoropropane Commercially available epoxidized polybutadiene (from Nisso Company, 8% epoxidation of the 90% vinyl pendent groups) was blended with 20% of 2,2-bis(4-epoxyphenyl)hexafluoropropane prepared as in Example 3 and then cured inside a mold with 4% 1,2,3,6-tetrahydrophthalic anhydride and 1% dicumyl peroxide according to a standard multi-stage curing process to form a cured disc copolymer material.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein and is only limited by the following claims.

What is claimed is:

1. A diphenylhexafluoropropane compound having the formula:

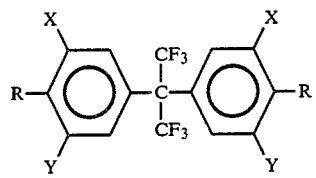

where R is an unsubstituted, or substituted alkylene, an epoxy, a silyl or alkoxysilyl group; and where X and Y are hydrogen or a halogen.

2. A diphenylhexafluoropropane compound according to claim 1 where X is a halogen and Y is hydrogen.

3. A diphenylhexafluoropropane compound according to claim 1 where R is vinyl, $\beta$-chlorovinyl, $\beta$-methylvinyl, ($\beta$-acetoxy)vinyl, $\beta$-phenylvinyl, $\beta,\beta$-dimethylvinyl, $\alpha$-chlorovinyl, or ($\beta$-methoxycarbonyl-$\beta$-methyl)vinyl.

4. A diphenylhexafluoropropane compound according to claim 1 where R is an alkylene group having from 1 to 4 carbon atoms.

5. A diphenylhexafluoropropane compound according to claim 1 where R is trimethylsilyl.

6. A diphenylhexafluoropropane compound according to claim 1 where R is an epoxy group having from 1 to 4 carbon atoms.

* * * * *